US011232868B1

United States Patent
(12) United States Patent
Sutherland et al.

(10) Patent No.: US 11,232,868 B1
(45) Date of Patent: Jan. 25, 2022

(54) MACHINE LEARNING-BASED SURGICAL INSTRUMENT CHARACTERIZATION

(71) Applicant: OrbSurgical Ltd., Calgary (CA)

(72) Inventors: Garnette Sutherland, Calgary (CA); Amir Baghdadi, Calgary (CA); Rahul Singh, Calgary (CA); Hamidreza Hoshyarmanesh, Calgary (CA); Sanju Lama, Calgary (CA)

(73) Assignee: OrbSurgical Ltd., Calgary (CA)

( * ) Notice: Subject to any disclaimer, the term of this patent is extended or adjusted under 35 U.S.C. 154(b) by 0 days.

(21) Appl. No.: 17/318,975

(22) Filed: May 12, 2021

(51) Int. Cl.
*G16H 50/70* (2018.01)
*G16H 40/67* (2018.01)
(Continued)

(52) U.S. Cl.
CPC ............. *G16H 50/70* (2018.01); *A61B 17/28* (2013.01); *A61B 34/30* (2016.02); *A61B 90/37* (2016.02);
(Continued)

(58) Field of Classification Search
CPC ........ G16H 50/70; G16H 40/67; G16H 15/00; G16H 40/20; G16H 20/40; G16H 70/20;
(Continued)

(56) References Cited

U.S. PATENT DOCUMENTS

2014/0058528 A1* 2/2014 Contreras-Vidal .... A61B 5/291 623/25
2019/0125455 A1* 5/2019 Shelton, IV ........... A61B 34/30
(Continued)

FOREIGN PATENT DOCUMENTS

JP 2019093472 A * 6/2019 ............. B25J 9/163
KR 101840833 B1 * 3/2018

OTHER PUBLICATIONS

Mozaffari, Ahmad; Behzadipour, Saeed; Kohani, Mehdi. "Identifying the tool-tissue force in robotic laparoscopic surgery using neuro-evolutionary fuzzy systems and a synchronous self-learning hyper level supervisor."Applied Soft Computing 14: 12-30. Elsevier. (Jan. 2014). (Year: 2014).*

(Continued)

*Primary Examiner* — Linh Giang Le
(74) *Attorney, Agent, or Firm* — Jones Day

(57) ABSTRACT

Data is received that is generated by at least one sensor forming part of a surgical instrument. The sensor(s) on the surgical instrument can characterize use of the surgical instrument in relation to a patient. A force profile segmentation model can construct a force profile using the received data. The force profile includes a plurality of force patterns. The force profile segmentation model includes at least one first machine learning trained using historical surgical instrument usage data. In addition, a plurality of features are extracted from the received data. Thereafter, one or more attributes characterizing use of the surgical instrument are determined by a force profile pattern recognition model using the constructed force profile and the extracted features. The force profile pattern recognition model includes at least one second machine learning model. Data characterizing the determination can be provided (e.g., displayed to a surgeon, etc.).

30 Claims, 9 Drawing Sheets

(51) Int. Cl.

| | |
|---|---|
| ***G16H 50/20*** | (2018.01) |
| ***G16H 70/20*** | (2018.01) |
| ***G16H 40/40*** | (2018.01) |
| ***G16H 40/20*** | (2018.01) |
| ***G06K 19/07*** | (2006.01) |
| ***G16H 15/00*** | (2018.01) |
| ***G16H 20/40*** | (2018.01) |
| ***H04L 29/06*** | (2006.01) |
| ***A61B 34/30*** | (2016.01) |
| ***A61B 17/28*** | (2006.01) |
| ***A61B 90/00*** | (2016.01) |
| ***A61B 90/98*** | (2016.01) |
| ***G06N 20/00*** | (2019.01) |
| *G06F 3/14* | (2006.01) |
| *A61B 17/00* | (2006.01) |

(52) U.S. Cl.

CPC .......... *A61B 90/98* (2016.02); *G06K 19/0723* (2013.01); *G06N 20/00* (2019.01); *G16H 15/00* (2018.01); *G16H 20/40* (2018.01); *G16H 40/20* (2018.01); *G16H 40/40* (2018.01); *G16H 40/67* (2018.01); *G16H 50/20* (2018.01); *G16H 70/20* (2018.01); *H04L 63/0421* (2013.01); *A61B 2017/00057* (2013.01); *A61B 2017/00075* (2013.01); *A61B 2090/064* (2016.02); *A61B 2090/372* (2016.02); *G06F 3/14* (2013.01)

(58) Field of Classification Search

CPC ........ G16H 40/40; G16H 50/20; A61B 34/30; A61B 90/98; A61B 90/37; A61B 17/28; A61B 2090/372; A61B 2090/064; A61B 2017/00075; A61B 2017/00057; G06K 19/0723; G06N 20/00; H04L 63/0421; G06F 3/14

See application file for complete search history.

(56) References Cited

U.S. PATENT DOCUMENTS

| | | | | |
|---|---|---|---|---|
| 2020/0082934 | A1 * | 3/2020 | Venkataraman ....... | G16H 40/20 |
| 2020/0367974 | A1 * | 11/2020 | Khalid ..................... | G06N 3/08 |

OTHER PUBLICATIONS

Naryan et. al. "Developing a novel force forecasting technique for early prediction of critical events in robotics." PLoS ONE 15.5: e0230009. Public Library of Science. May 7, 2020 (Year: 2020).*

* cited by examiner

MACHINE LEARNING-BASED SURGICAL INSTRUMENT CHARACTERIZATION

TECHNICAL FIELD

The subject matter described herein relates to machine learning-based techniques for characterizing the use of sensor-equipped surgical instruments to improve patient outcomes.

BACKGROUND

According to the World Health Organization (WHO), surgical procedures lead to complications in 25% of patients (around 7 million annually) among which 1 million die. Among surgical tasks responsible for error, tool-tissue force exertion is a common variable. Surgical simulation has shown that more than 50% of surgical errors are due to the inappropriate use of force contributing to an annual cost of over $17 billion in the USA alone.

SUMMARY

In a first aspect, data is received that is generated by at least one sensor forming part of a surgical instrument. The surgical instrument can take various forms including being handheld, fully manual, and/or at least partially robotic. The sensor(s) on the surgical instrument can characterize use of the surgical instrument in relation to a patient. A force profile segmentation model can construct a force profile using the received data. The force profile includes a plurality of force patterns. The force profile segmentation model includes at least one first machine learning trained using historical surgical instrument usage data. In addition, a plurality of features are extracted from the received data. Thereafter, one or more attributes characterizing use of the surgical instrument are determined by a force profile pattern recognition model using the constructed force profile and the extracted features. The force profile pattern recognition model includes at least one second machine learning model. Data characterizing the determination can be provided.

The sensor(s) forming part of the surgical instrument can take various forms including one or more of: an identification sensor, a force sensor, a motion sensor, a position sensor, an accelerometer, or an optical sensor. In one variation, the surgical instrument are forceps with right and/or left prongs having a sensor embedded or affixed thereto.

The sensor(s) forming part of the surgical instrument can generate different types of data including time-series based data characterizing use of the surgical instrument.

Noise in the received data can be reduced prior to the extraction of the features and/or use by the force profile segmentation model.

Outliers in the received data can be removed prior to the extraction of the features and/or use by the force profile segmentation model.

The force profile segmentation model can include an encoder network followed by a decoder network.

At least a part of the received data can include a waveform such that the extracted features characterize one or more of: maximum, range, coefficient of variance, peak counts, peak values, cycle length, signal fluctuations, entropy, or flat spots.

The force profile pattern recognition model can include at least one neural network.

The data characterizing the determination can identify a surgical task performed using the surgical instrument.

The data characterizing the determination can identify a skill level associated with use of the surgical instrument. The data characterizing the determination can identify a skill level associated with a particular surgical task using the surgical instrument.

At least one of the at least one first machine learning model and the at least one second machine learning model can be trained using data generated from a single type of surgical instrument and/or from a single surgeon. Further, at least one of the at least one first machine learning model and the at least one second machine learning model can be trained using data generated from a plurality of surgeons.

The surgical instrument can include an identification element. Such an identification element can be associated with one of a plurality of machine learning models such that at least one of the at least one first machine learning model and the at least one second machine learning model is selected from the plurality of available machine learning models based on the associating. The identification element can take various forms including a radio frequency identification (RFID).

Providing data characterizing the determination can include one or more of: causing the data characterizing the determination to be displayed in an electronic visual display, storing the data characterizing the determination in physical persistence, loading the data characterizing the determination in memory, or transmitting the data characterizing the determination to a remote computing system.

The provided data can characterize various actions including a completion time for a surgical task, a range of force applications in connection with a surgical task, a force variability index, or a force uncertainty index compared to one or more other surgical instrument users.

The provided data can include conveying feedback to a user of the surgical instrument. The feedback can take various forms including one or more of haptic, visual, or audio feedback.

The feedback can be conveyed on a heads-up display worn or in view of a user of the surgical instrument.

At least one of the force profile segmentation model or the force profile recognition model can be trained locally on an endpoint computing instrument executing both such models. In other variations, at least one of the force profile segmentation model or the force profile recognition model is trained at least on part by a cloud-based computing service.

In some variations, feature extracted from the data are anonymized and then encrypted. The encrypted, anonymized features can be transmitted to a remote computing system to train one or more models corresponding to at least one of the force profile segmentation model or the force profile recognition model. The features can be anonymized using various techniques including using k-anonymity privacy. Various encryption technologies can be utilized including homomorphic encryption In some variations, at least one of the force profile segmentation model or the force profile pattern recognition model through federated learning using a combination of an edge device executing such models and a cloud-based system.

In an interrelated aspect, one or more data streams are received that generated by at least one sensor forming part of a surgical instrument. The at least one sensor characterizes use of the surgical instrument by a surgeon in relation to a patient. Thereafter, a force profile is constructed by a force profile segmentation using the received data streams. The force profile includes a plurality of force patterns and the force profile segmentation model can include at least one first machine learning trained using historical surgical instrument usage data. A plurality of features can be continually extracted from the received data. Based on these features, one or more attributes characterizing use of the surgical instrument can be determined by a force profile pattern recognition model. The force profile pattern recognition model can include at least one second machine learning model. Real-time feedback can be provided to the surgeon based on the one or more determined attributes characterizing use of the surgical instrument.

In a further interrelated aspect, a system includes a plurality of edge computing devices and a cloud-based system. The plurality of edge computing devices are each configured to receive one or more data streams generated by at least one sensor forming part of a respective surgical instrument. The at least one sensor characterizing use of the respective surgical instrument by a particular surgeon in relation to a particular patient, each of the edge computing devices executing a local force profile segmentation model and a force profile recognition model. The cloud-based system is configured for training and updating each of a master force profile segmentation model and a master force profile pattern recognition model based on model parameter data received from the plurality of edge computing devices which has been anonymized and encrypted using homomorphic encryption prior to it being transmitted over a network by the edge computing devices. The cloud-based system sends updates over the network to each of the respective local force profile segmentation models and to each of the force profile recognition models.

Non-transitory computer program products (i.e., physically embodied computer program products) are also described that store instructions, which when executed by one or more data processors of one or more computing systems, cause at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DETAILED DESCRIPTION

The current subject matter is directed to enhanced techniques and systems for monitoring or otherwise characterizing use of a surgical instrument during one or more surgical procedures. While the current subject matter is described, as an example, in connection with sensor-equipped forceps, it will be appreciated that the current subject matter can also be used with other sensor-equipped surgical instruments including, electrosurgical (bipolar or monopolar) or otherwise, without limitation, cutting instruments, grasping instruments, and/or retractors.

As noted above, the current subject matter can be used with sensor-equipped forceps such as that described in U.S. Pat. Pub. No. 20150005768A1 and entitled: "Bipolar Forceps with Force Measurement", the contents of which are hereby incorporated by reference. The surgical instruments used herein can include one or more sensors such as an identification sensor (e.g., RFID, etc.), force sensors, motion sensors, position sensors. The data generated from such sensors can be connected to a developed signal conditioning unit interfaced through a software with machine learning algorithm (federated and global) deployed to the cloud (or in some cases executing at a local endpoint). The machine learning algorithms can interface with a unique federated learning architecture such that tool, sensor and surgeon specific data, are recognized, segmented and analyzed (signal, task, skill, pattern (position, orientation, force profile)—all based on sensor signal), such that high fidelity feedback can be generated and provided in real-time (warning) or performance reporting (via secure application or online user profile).

Figure 1:
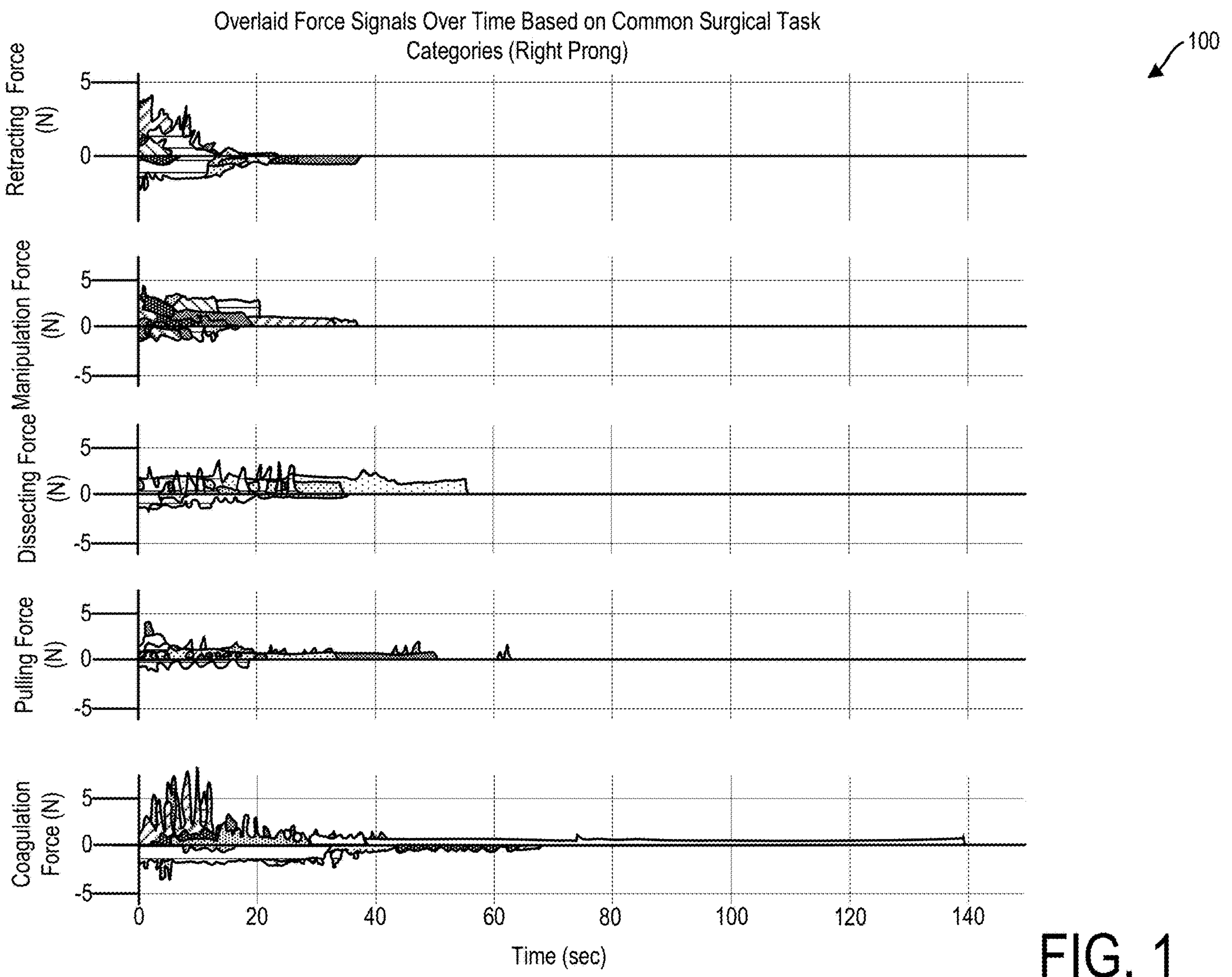
FIG. 1 is a first diagram illustrating force signals generated from a sensor-equipped surgical instrument over five different surgical tasks.

For data modeling to validate and/or otherwise inform the advances provided herein, 50 neurosurgery cases that used sensor-equipped forceps (herein after sensor-equipped forceps) for tumor resection of various types in adult patients including meningioma, glioma, hemangioblastoma, and schwannoma was employed. Twelve surgeons performed the cases, which included one Expert surgeon with 30+ years of experience and 11 Novice surgeons ranging across 3 levels of post-graduate years (PGY) 1-2 (n=4), 3-4 (n=3) and >4 years (n=4). The surgical team adopted and used the sensor-equipped forceps system, similar to and instead of, a conventional bipolar forceps. The recorded data includes time-series of tool-tissue interaction force through sensor-equipped forceps, transcribed voices of the surgical team, and microscopic video data to label the training dataset for surgical error incidents and neurosurgical maneuvers categorized into 5 main different tasks, i.e. (1) coagulation (cessation of blood loss from a damaged vessel), (2) dissection (cutting or separation of tissues), (3) pulling (moving and retaining tissues in one direction), (4) retracting (grasping and retaining tissue for surgical exposure), and (5) manipulating (moving cotton or other non-tissue objects). The added advantage was the provision of real-time tool-tissue force measurement, display, and recording. A snapshot of aggregated force data over the 50 cases of neurosurgery is illustrated in diagram 100 of FIG. 1. The graph in FIG. 1 highlights the differences in completion time and range of forces across the 5 surgical tasks. In particular, FIG. 1 illustrates sensor-equipped forceps timeseries data of the Right prong across the 5 surgical tasks of Retracting, Manipulation, Dissecting, Pulling, and Coagulation overlaid for 50 cases. Differences in the range and duration of force are shown in the overlaid data profiles.

A data management framework as used herein can be include a curing pipeline and reporting structure incorporating a data ingestion point where the segmented force profiles representing a consolidated period of force application in a specific surgical task was imported. The force segments were identified through the processing of operating room voice data and were concatenated into a structured dataframe containing various information including timestamp, surgeon and experience level, surgical task type, and high/low force error or bleeding instances. In the next step, 37 time-series-related features were calculated from the manually segmented task force data in each prong among which a subset of 25 with a combination of average, minimum, or maximum value of features for each prong was selected for the subsequent analysis based on statistical tests to monitor their representation power in different surgeon skill and task categories. The aim was to have the best explain of patterns and behaviors for force profiles over the timespan of each data segment. These time-series features included:

Force Duration: duration of force application in one task segment.

Force Average: average of force values in one task segment.

Force Max: maximum of force values in one task segment.

Force Min: minimum of force values in one task segment.

Force Range: range of force values in one task segment.

Force Median: median of force values in one task segment.

Force SD: standard deviation of force values in one task segment.

Force CV: coefficient of variation of force values in one task segment.

Force Mean CI (0.95): confidence interval on the mean with 95% probability.

Force Data Skewness: the extent to which the force data distribution deviates from a normal distribution.

Force Data Skewness 2SE: the significance of skewness in force data based on dividing by 2 standards errors (significant when >1).

Force Data Kurtosis: the extent to which the force data distribution is tailed in a normal distribution.

Force Data Kurtosis 2SE: the significance of kurtosis in force data based on dividing by 2 standards errors (significant when >1).

Force Data Normality: Shapiro-Wilk test of normality in force data distribution.

Force Data Significance of Normality: significance of Shapiro-Wilk test of normality.

Force Peak Value: peak force value in one task segment.

Force Peak Counts: number of force peaks in one task segment.

1st Derivative SD: standard deviation for the first derivative of the force signal in one task segment.

Force Signal Flat Spots: maximum run length for each section of force time-series when divided into ten equal-sized intervals.

Force Signal Frequency: dominant time-series harmonics extracted from Fast Fourier Transform (FFT) of force value in one task segment.

Force Cycle Length: average time length of force cycles in one task segment.

Force Signal Trend: force time-series trend in one task segment.

Force Signal Fluctuations: force time-series fluctuation index in one task segment.

Force Signal Spikiness: force time series spikiness index (variance of the leave-one-out variances of the remainder component) in one task segment.

Force Signal Linearity: force time-series linearity index (from Teräsvirta's nonlinearity test) in one task segment.

Force Signal Stability: force time-series stability index (variance of the means) in one task segment.

Force Signal Lumpiness: force time-series lumpiness index (variance of the variances) in one task segment.

Force Signal Curvature: force time-series curvature index in one task segment (calculated based on the coefficients of an orthogonal quadratic regression).

Force Signal Mean Shift: force time-series largest mean shift between two consecutive windows in one task segment.

Force Signal Variance Shift: force time-series largest variance shift between two consecutive windows in one task segment.

Force Signal Divergence: force time-series divergence index in one task segment (largest shift in Kulback-Leibler divergence between two consecutive windows).

Force Signal Stationary Index: force time-series stationary index around a deterministic trend in one task segment (based on Kwiatkowski-Phillips-Schmidt-Shin (KPSS) unit root test with linear trend and lag one).

Force Signal Entropy: force time-series forecastability in one task segment (low values indicate a high signal-to-noise ratio).

First Autocorrelation Minimum: time of first minimum of the autocorrelation function in force time-series signal from one task segment.

First Autocorrelation Zero: time of first zero crossing of the autocorrelation function in force time-series signal from one task segment.

Autocorrelation Function E1: first autocorrelation coefficient from force time-series signal in one task segment.

Autocorrelation Function E10: sum of the first ten squared autocorrelation coefficients from force time-series signal in one task segment.

To find accurate force peaks within each task segment, the signals were smoothed by passing through a digital 4th order Butterworth low-pass filter with a cutoff frequency of 0.1 Hz. Further, the outlier segmented data were identified based on 1st and 99th percentiles of either maximum force, minimum force, or task completion time from all trials of the expert surgeon as <1% error was assumed to occur by experienced surgeons. The force segments for which the maximum force peak, minimum force valley, or task completion time exceeded the upper threshold (99th percentile) or fell short of the lower threshold (1st percentile) were labeled as outliers and removed (~11%).

Figure 2:
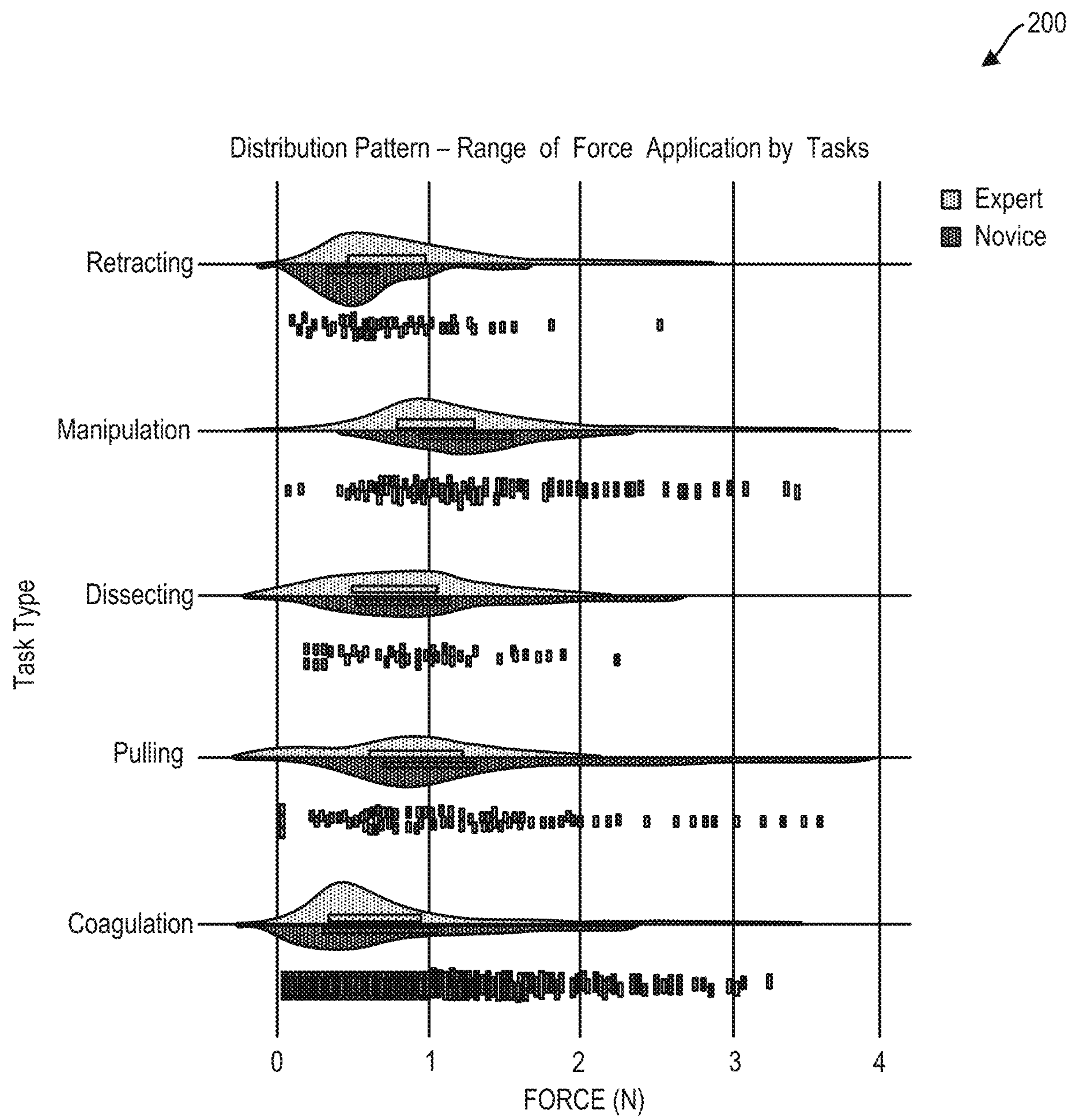
FIG. 2 is a second diagram illustrating force signals generated from a sensor-equipped surgical instrument over five different surgical tasks.

Interactive figures of the force time-series features extracted from all 50 cases were categorized in 5 different tasks. FIG. 2 is a diagram 200 illustrating a sample result. FIG. 2 shows the relationship between different skill levels and across different tasks. In particular, FIG. 2 illustrates aggregative data distribution of both Expert and Novice surgeons across the surgical tasks for each time-series extracted feature.

Again, to validate the current innovations, data was analyzed prior to exploring machine learning models for a better behavior understanding of the force profiles. Summary statistics were extracted for each task and surgeon experience that included the number of force segments and mean (SD) of the force features across all available segments.

The number of force segments were 2085 for Coagulation (Expert: 1108; Novice: 977), 303 for Pulling (Expert: 192; Novice: 111), 296 for Manipulation (Expert: 210; Novice: 86), 89 for Dissecting (Expert: 64; Novice: 25), and 122 for Retracting (Expert: 71; Novice: 51), with a total value of 1645 for Expert and 1250 for Novice surgeons. The mean (SD: Standard Deviation) for Force Duration in Coagulation was 12.1 (7.2) seconds—around 58% higher than the average of completion time in other tasks—while the completion time in Pulling, Manipulation, Dissecting, and Retracting tasks were 7.6 (5.3), 5.4 (2.5), 10.1 (8.6), and 7.6 (5.1) seconds, respectively. The mean (SD) for Force Range in Manipulation was 1.2 (0.5) N—around 52% higher than the average of completion time in other tasks—while the range of forces in Coagulation, Pulling, Dissecting, and Retracting tasks were 0.7 (0.5), 1 (0.6), 0.9 (0.5), and 0.7 (0.4) N, respectively. For presenting the level of force variability, Standard Deviation was calculated across the tasks and surgeons. The mean (SD) across all tasks were 0.23 (0.14) for Expert and 0.27 (0.14) for Novice surgeons. For materializing the unsafe force application risk, Force Peak Values were identified across the tasks and surgeons. The mean (SD) across all tasks were 0.35 (0.27) for Expert and 0.39 (0.29) for Novice surgeons. Level of Force Signal Entropy was used to measure the level of randomness in force application for among different surgical experience. Mean (SD) of this feature for Expert surgeon was 0.67 (0.09) and for Novice surgeons was 0.65 (0.07).

To understand the pattern of force data in various conditions under investigation, independent measures two-way ANOVA was performed that simultaneously evaluates the effect of experience and task type as two different grouping variables on the continuous variable of tool-tissue interaction force. The results showed significant difference between experience levels in various features including Force Maximum (p=0.000), Force Range (p=0.001), Force Standard Deviation (p=0.000), Force Distribution Kurtosis (p=0.001), Force Peak Values (p=0.001), Force Flat Spots (p=0.000), Force Signal Frequency (p=0.001), Force Signal Fluctuations (p=0.02), Force Signal Stability (p=0.001), Force Signal Mean Shift (p=0.000), and Force Signal Entropy (p=0.001). Among various tasks, several features were significantly different, e.g., Force Duration (p=0.000), Force Average (p=0.000), Force Maximum (p=0.000), Force Range (0.000), Force Peak Values (p=0.000), Force Peak Counts (p=0.000), Force Signal Flat Spots (p=0.000), Force Signal Frequency (p=0.000), Force Signal Fluctuations (p=0.000), and Force Signal Stability (p=0.000), and Force Signal Curvature (p=0.000). The results showed no significant difference for Force Coefficient of Variation and Force Signal Cycle Length among tasks, experience levels, and their interaction.

Based on the ANOVA test results, a subset of features was extracted for developing machine learning models. In this subset, Force Duration, Force Minimum, Force Coefficient of Variance, Force Data Skewness, Force Data Skewness 2SE. 1st Derivative SD, Force Peak Counts, Force Cycle Length, Force Signal Spikiness, Force Signal Stationary Index, First Autocorrelation Zero, and Autocorrelation Function E10 were excluded. In addition, the surgical tasks were classified as 5 main categories of Retracting [the tumor or tissues], Manipulation [of cotton], Dissecting [the tumor or tissues], Pulling [the tumor or tissues], and Coagulation [the vessels/veins in tumor or tissues].

During the initial model developments, experiments were conducted for skill classification based on the available data of 50 cases using a support vector machine (SVM) model on 25 extracted features after dimensionality reduction by principal component analysis (PCA) showed the highest area under the curve (AUC) of 0.65, training accuracy of 0.60, testing accuracy of 0.62 with the sensitivity of 0.66 and specificity of 0.57. The optimal model parameters were radial basis kernel function with both cost and gamma values of $0.1\times10^{0.1}$.

In addition, a deep learning model (e.g., neural network, etc.) based on long short-term memory (LSTM) was crafted that has an input layer with 100 inputs, a single layer hidden layer with 100 LSTM neurons, a dropout layer with the ratio of 0.5 to reduce overfitting of the model to the training data, a dense fully connected layer with 100 neurons and ReLU activation function to interpret the extracted features by the LSTM hidden layer, and an output layer with Softmax activation to make predictions for the 5 classes. The optimizer used to train the network was the adam version of stochastic gradient descent with categorical cross entropy as the loss function. The network was trained for 1000 epochs and a batch size of 20 samples was used for the optimal results that showed mean (SD) loss of 0.598 (0.001), mean (SD) accuracy of 0.828 (0.001), and mean squared error of 0.055 (0.001).

The data framework can include a HIPAA and PIEPDA compliant cloud architecture for retaining and processing the intraoperative de-identified data through a cloud platform with secure authentication and an interactive web/mobile application which interfaced with a progressive web application (PWA) to make it installable on mobile devices. Data characterizing the use of the surgical instruments can be displayed in various dashboards rendered in one or more graphical user interface. The dashboards can be personalized for data scientists as well as each surgeon's view who need to login through their personified credentials to perform data analysis or track their performance by comparing to expert surgeon(s) in the "Expert Room" (FIGS. 3-8).

The application can render multiple graphical user interfaces for different aspects including for 1) For both data scientist and surgeon: Geospatial Information for sensor-equipped forceps cases across the world with multiple choice selection lists and interactive maps to display the information in a searchable table; 2) For both data scientist and surgeon: Surgical Force Data for visualizing different engineered features across each task through interactive distribution plots showing detailed statistics for Expert or Novice surgeons to compare and reproduce each force segment through mouse hover and click; 3) For surgeon: Performance Comparison Dashboard for tracking of individual performance over time characterized by task completion time, range of force application, force variability index, and force uncertainty index (level of entropy in time series data) compared to the average and range of an expert surgeon; 4) For data scientist: Skill Prediction Tool for step-by-step training and testing of models with parameter fine-tuning and generating results to distinguish surgical expertise; and 5) For data scientist: Task Recognition Tool for visualizing, training and testing of models with parameter fine-tuning and generating results to perform surgical task classification. Through this platform, personalized performance data will be available for each surgeon through their user-specific account to view, compare, or share their case data with other colleagues in the field.

Figure 3:
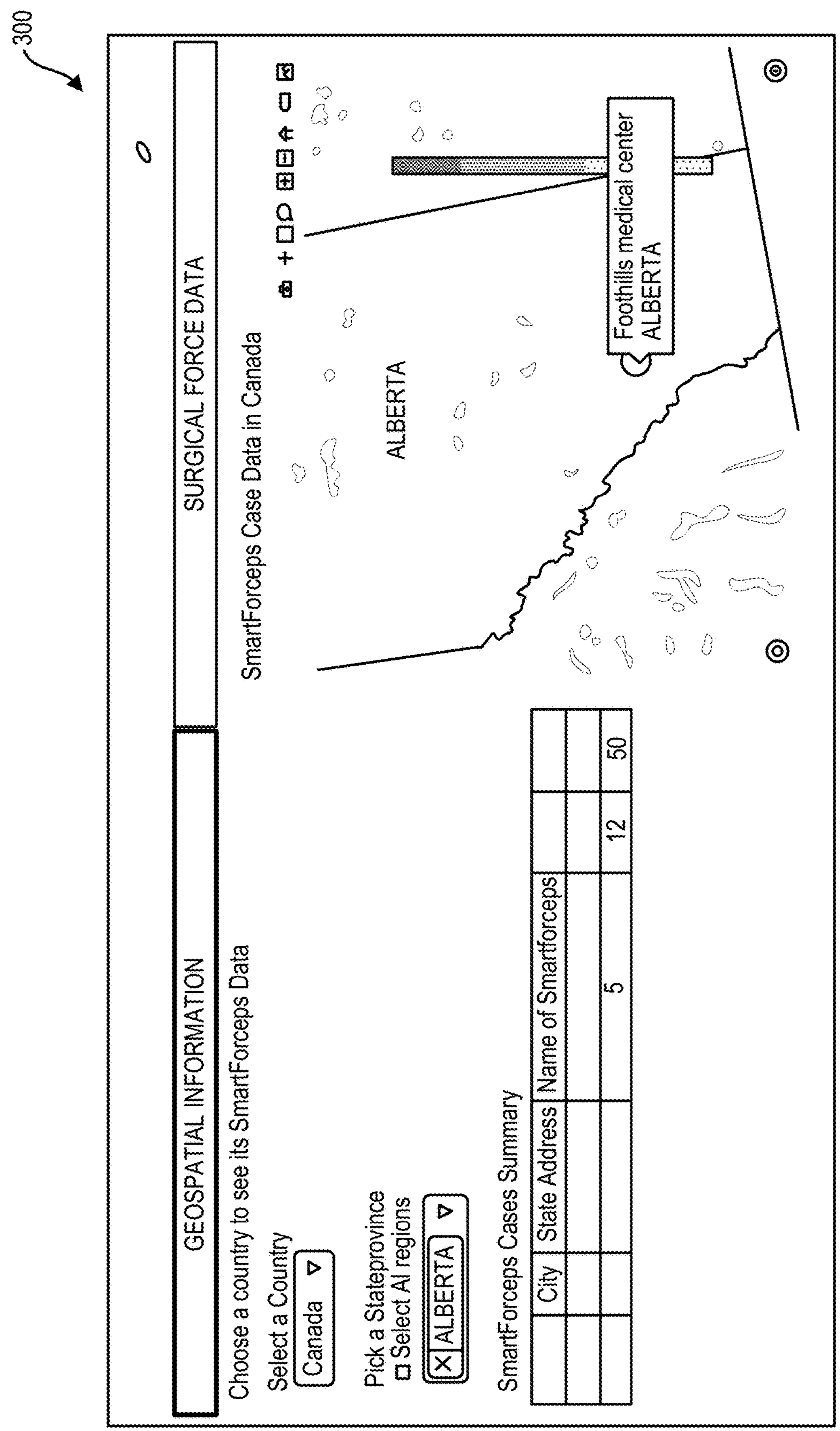
FIGS. 3-7 are diagrams illustrating views of a graphical user interface dashboard characterizing use of one or more surgical instruments.

With reference to diagram 300 of FIG. 3, a geospatial information tab can include an interactive map to select each surgical center along with dropdown lists to adjust the map view based on each country and region selection. The case summary including hospital information, number of sensor-equipped forceps systems available, cases completed, and active surgeons appears in an interactive table.

Figure 4:
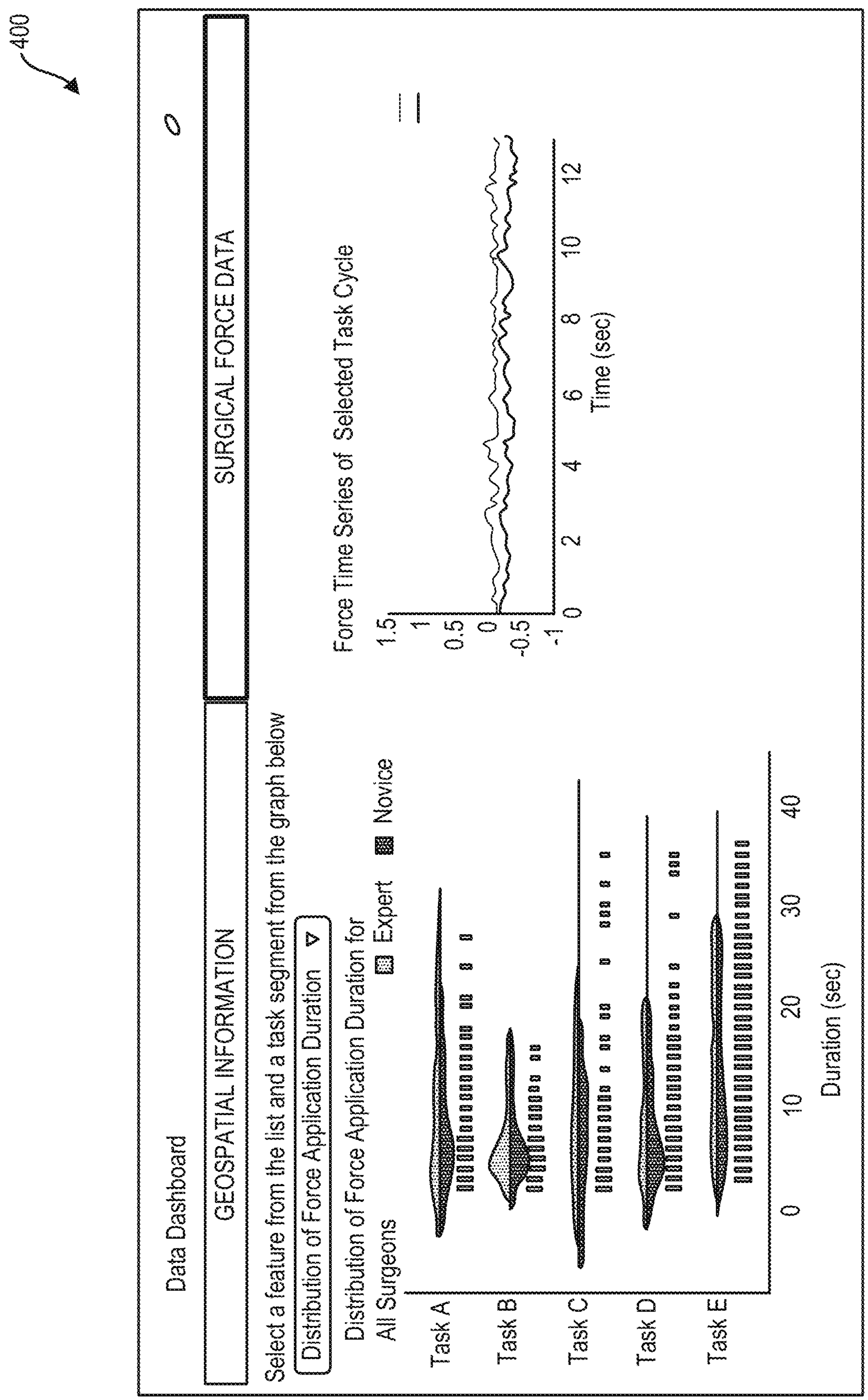

With reference to diagram 400 of FIG. 4, a surgical force data tab includes interactive graphics that show aggregative data distribution of both Expert and Novice surgeons across the surgical tasks based on a feature selected from the dropdown menu (left column chart). The actual force profiles for left (red time-series plot) and right (blue time-series plot) prong of sensor-equipped forceps (right column chart) can be shown by hover+click on each data point of the violin distribution plots.

Figure 5:
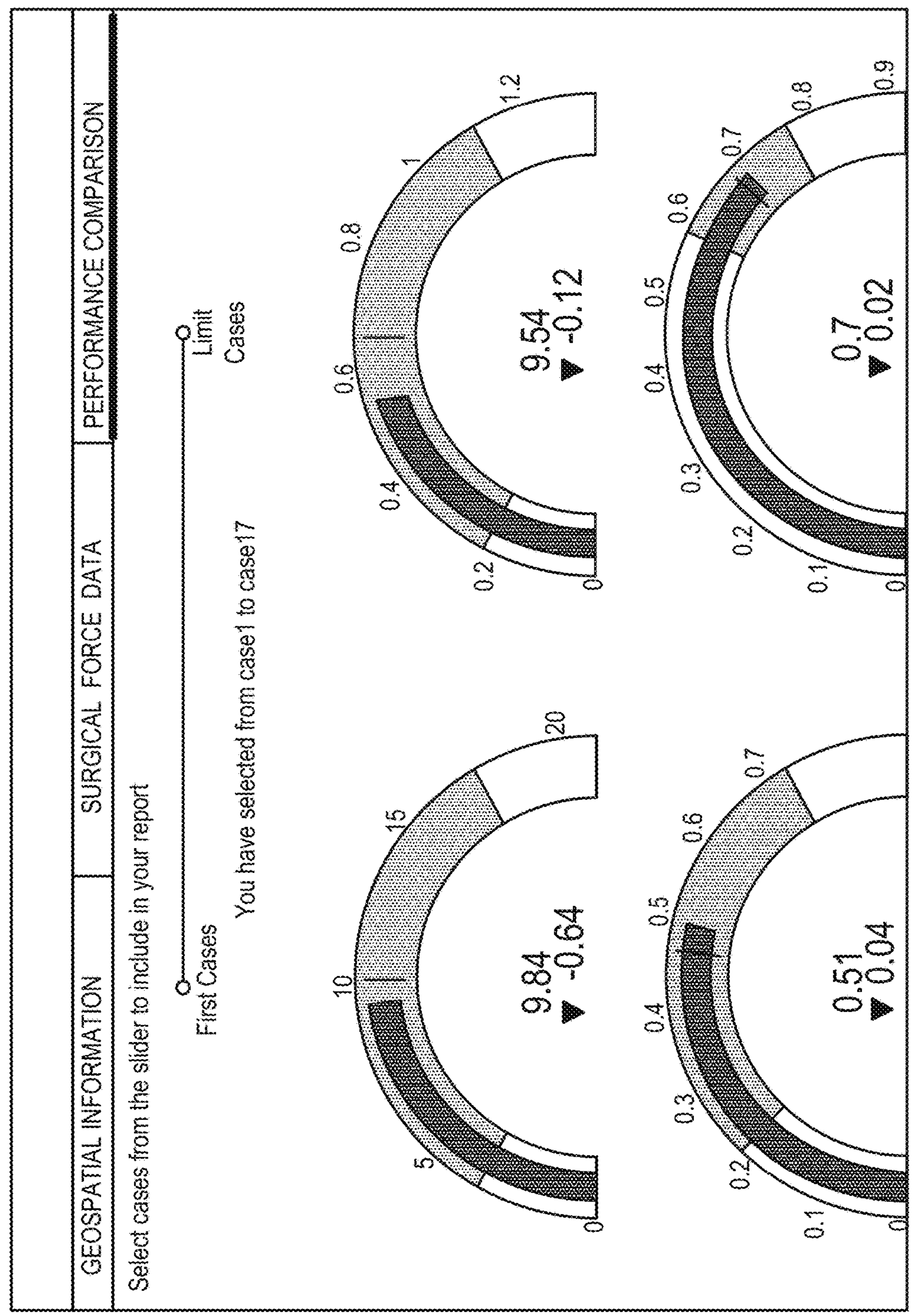

FIG. 5 is a diagram 500 illustrating a data analytics dashboard in "Surgeon" view. The current view includes three tabs of "Geospatial Information", "Surgical Force Data", and "Performance Comparison Dashboard". These charts have fully interactive capability including zoom, pan, download, etc. This figure, as an example, shows the over-time performance report (with the slide bar at the top to select range of cases) for a Novice surgeon with PGY >4. The name is deidentified for privacy reasons. The gauge charts show the performance compared to the Expert surgeon.

Figure 6:
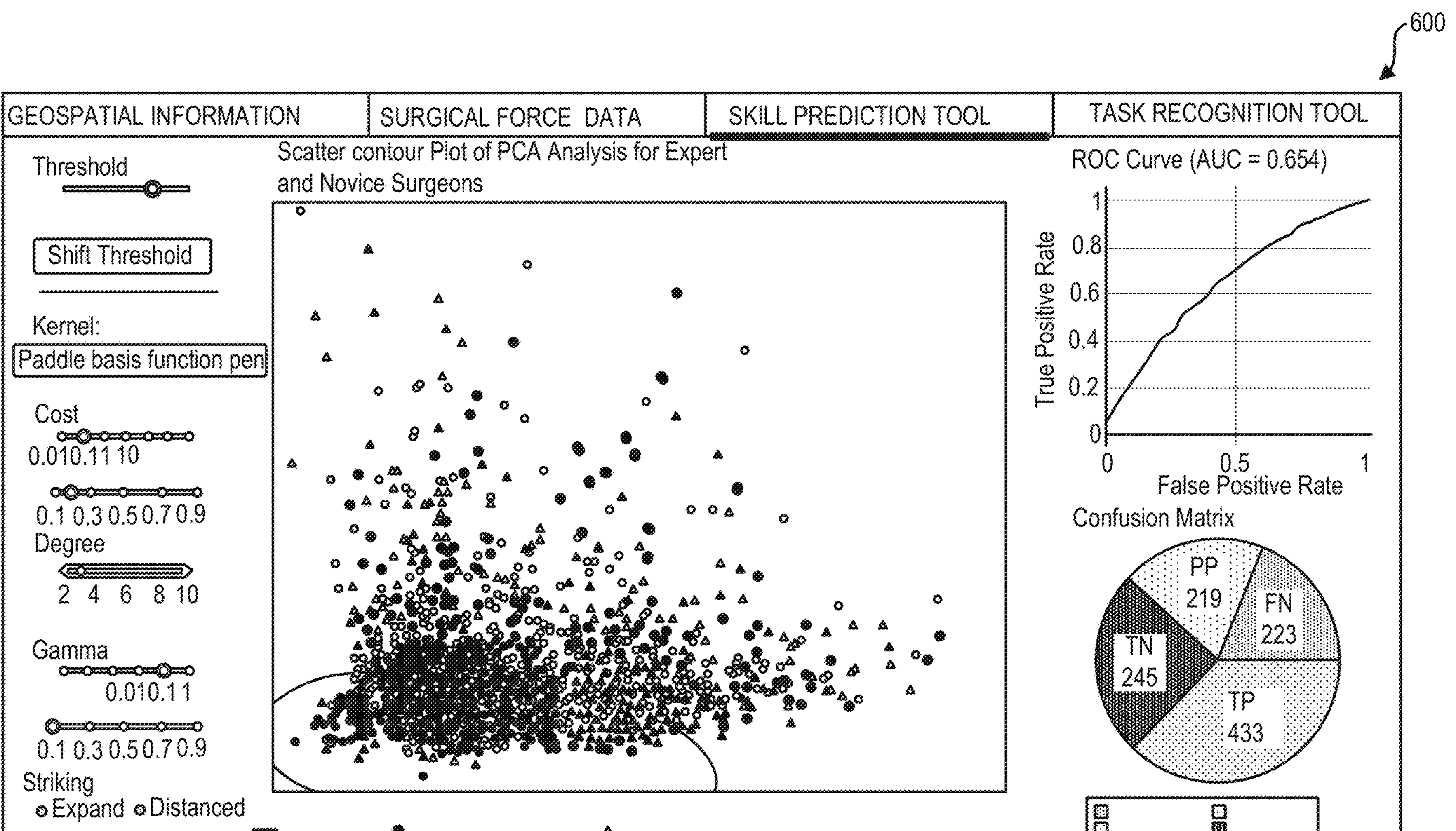

FIG. 6 is a diagram 600 illustrating a graphical user interface view corresponding to a task recognition tool tab which incorporates an interactive tool for a data scientist to view the reduced feature map after applying dimensionality reduction (e.g., principal component analysis, etc.) on the full feature set portraying the force profiles of sensor-equipped forceps and characterizing the surgical skill levels (the scatter contour plot in the middle column—purple points belong to Novice and green points to Expert; the circular and triangular points indicate training and testing data), interactive panel for selecting the machine learning model (e.g., SVM, etc.) parameters (left column), and graphical results of the machine learning model including ROC curve and confusion matrix (right column) along with the training and testing accuracies (middle column—under the scatter contour plot).

Figure 7:
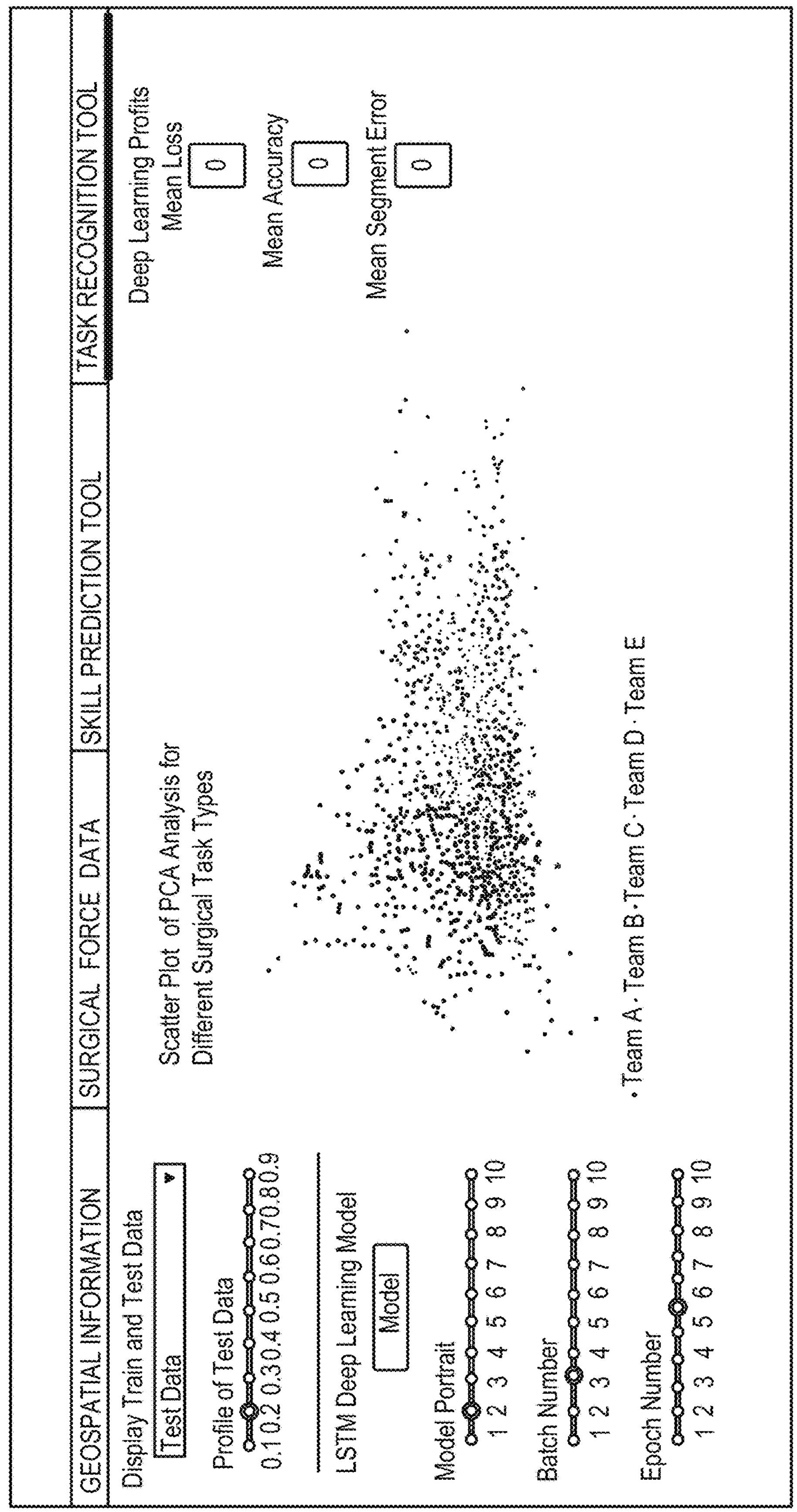

FIG. 7 is a diagram 700 that includes a graphical user interface view of a skill prediction tool tab that incorporates an interactive tool for a data scientist to view the reduced feature map after applying dimensionality on the full feature set portraying the force profiles of sensor-equipped forceps marked by different colors for each surgical task (the scatter contour plot in the middle column), interactive panel for selecting the parameters and running the LSTM model (left column), and the results of the deep learning model on the actual force profile in terms of mean loss, mean accuracy, and mean squared error (right column).

To quantify the behavior of force profiles for pattern recognition and performance analysis, one or more machine-learning models can be provided for segmenting and recognizing the patterns of intra-operative force profiles. Deep learning models can be used that include multiple layers of feature representation as a stacked neural network. Such a model can be configured so that it does not make any assumptions about the underlying pattern in the force data so that it is robust to noise. This framework can model a more complex structure in non-stationary time-series data, where data characteristics including mean, variance, and frequency change over time.

Figure 8:
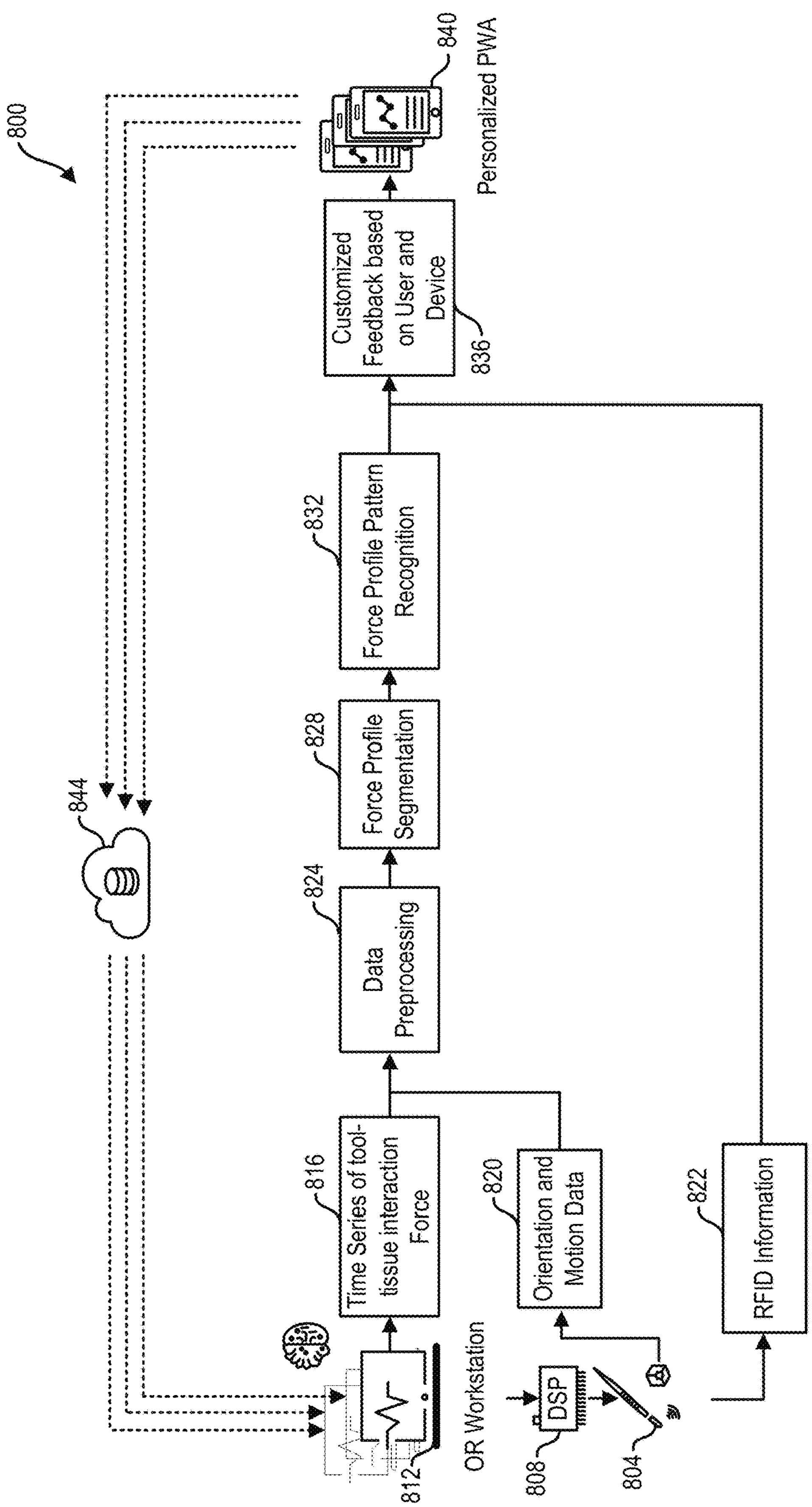
FIG. 8 is a diagram illustrating a sample architecture for characterizing the use of a surgical instrument using machine learning.

FIG. 8 is an example architecture diagram 800 which comprises a sequence two or more machine learning models that can interact with a surgical instrument. In this example, the surgical instrument is a sensor-equipped forceps 804; however, it will be appreciated that other types of surgical instruments can be used. In addition, while the example of FIG. 8 includes two machine learning models executing in sequence, it will be appreciated that a different ensemble and/or architecture of two or more machine learning models can be used depending on the desired configuration including, for example, the type of data being generated by the surgical instrument and/or other types of complementary data being generated by other medical devices or instruments within a surgical setting (e.g., an operating room).

Referring again to FIG. 8, a surgical instrument 804 (i.e., a sensor-equipped surgical can communicate with one or more computing devices including an operating room workstation 812 by way of a communications interface 808 such as a digital signal processor (e.g., a DSP for conditioning data generated by strain gauge sensor). The surgical instrument 804 through its sensors, generates one or more data streams that characterize the use of the surgical instrument (in general and in relation to a patient). These data streams can take various forms and can be provided directly, or indirectly (e.g., via the operating room workstation 812) to a consuming application or process. A first data stream 816 can provide time-series data characterizing tool-tissue interaction force (e.g., derived from a strain gauge sensor on the surgical instrument 804, etc.). A second data stream 820 can provide data characterizing the orientation and motion of the surgical instrument 804 (e.g., derived from a inertial measurement unit sensor on the surgical instrument, etc.). In addition, identification information 822 can also be provided. This identification information can, for example, be derived from an RFID or similar sensor on the surgical instrument.

Data from the first and second data streams 816, 820 can be pre-processed in a variety of manners. Pre-processing can include labeling the data, filtering out noise, removing outliers, and/or extracting features from the data streams. The noise reduction can, for example, be performed using a Butterworth low-pass filter and outliers can be removed based on the 1st and 99th percentile thresholds of expert force profiles as <1% error was assumed to occur by experienced surgeons. Features that can be extracted include those referred to above as well as one or more of e.g., force maximum, range, coefficient of variance, peak counts and values, cycle length, signal fluctuations and entropy, and flat spots, and the like.

A first machine learning model 828 (e.g., a force profile segmentation model, etc.) can take the pre-processed data (i.e., the cleaned force time-series data, extracted features, etc.) to construct force profile comprising a plurality of force patterns. The first machine learning model 828 can take various forms and, in one example, can be a U-Net model comprising a convolutional encoder and decoder structure to capture the properties and reconstruct the force profile ($X\_in \in R\hat{}(S\_0 \times i \times C)$: S_0 fixed-length segment interval each containing i data points through C=2 channels for left and right prong) through a deep stack of feature maps followed by a mean-pooling-based classifier on point-wise confidence scores for interval-wise time series segmentation ($X\_(seg.) \in R\hat{}(S \times K)$: S final segment intervals containing K=2 segment classes, i.e. device on/off).

A second machine learning model 832 can characterize force profile pattern recognition. The output of this second machine learning model 832 can be used to directly or indirectly characterize surgical experience level. In other words, the output of the second machine learning model 832 can be used as part of an algorithm to classify surgeon experience level (i.e., novice, intermediate, and expert) and allocate surgical competency scores based on descriptive force patterns, high force error, low force error, variable force, and other unsafe force instances.

The second machine learning model 832 can, for example, be a neural network or ensemble of neural networks. In one variation, the second machine learning model 832 comprises a deep neural network model for time series classification based on InceptionTime 33 to obtain learned features that together with engineered features such as described above can be used in a logistic regression-based surgeon experience classification. The input to the network can be a segmented force time-series (X_(seg.) E R^(S×C): S segment intervals over C=2 channels of left and right prong data in sensor-equipped forceps). The network can comprise multiple layers including a bottleneck layer to reduce the dimensionality, a series of convolutional layers to learn the features followed by connection layers, and a max pooling layer. The output of the network can be probabilities of different classes, i.e., surgical proficiency scores.

In addition or in some variations, the output of the second machine learning model 832 can be used to identify or otherwise characterize surgical task type. This can be based on a time-series based surgeon activity recognition while performing a specific task (i.e., coagulation, dissection, pulling, retracting, and manipulating). A recurrent neural network based on LSTM can be used in this regard that includes an input layer for the segmented force data (X_(seg.) E R^(S×C)), hidden layers with ReLU activation to interpret the extracted features, and a dropout regularization layer, a ReLU activation layer, and an output layer with Softmax activation providing the probability distribution of each surgical task class. The network weights Θ which characterizes the behavior of transformations can be identified through nonlinear optimization methods e.g., gradient descent and adam, to minimize the loss function, e.g., categorical cross entropy, in the training data and backpropagation of error throughout the network for updating the weights.

The output of the first and second machine learning models 828, 832 can be used to provide feedback to the user of the surgical instrument 804 (e.g., a surgeon, etc.). The feedback can be provided in various manners including haptic, audio, visual (e.g., a heads up display, etc.) and/or on an endpoint computing device 940 (e.g., a mobile phone, a tablet, a computer, etc.). The real-time feedback can be generated after incorporating the sensory input data (IMU: orientation and motion details—Strain Gauge: tool-tissue interaction force—RFID: radio-frequency identification for the unique tool specs (tool type (forceps, dissector, suction device, etc.), tool length, tip size, calibration factor, manufacturing date, etc.)) into the first and second machine learning models 828, 832 and the output can be customized based on the user skill and tool type. The feedback can be provided, for example, when there is an unsafe event so that the surgeon can take appropriate remedial action.

The feedback provided by the current subject matter can take various forms and have different granularity. The output of one or more of the first and second machine learning models 828, 832 can be used to specify how a particular user is performing relative to their own past performance, how that particular user is performing relative to his or her peers within a particular group (e.g., hospital), how that particular user is performing across all surgeons, and the like. In some cases, there can be different levels/groupings such as trainee—master—peers and that these groups may have their own associated first and second machine learning models 828, 832 which are used to provide feedback (whether in real-time or post-surgery procedure).

One or more of the first and second machine learning models 828, 832 can be updated or otherwise trained using a federated learning procedure which utilizes data generated by multiple surgical instruments 804 across different users and/or across different locations. The machine learning model parameters transported to the cloud as part of the federated learning procedure 844 can be de-identified, encrypted (e.g., homomorphically encrypted, etc.) prior it to be being transported over the network.

Figure 9:
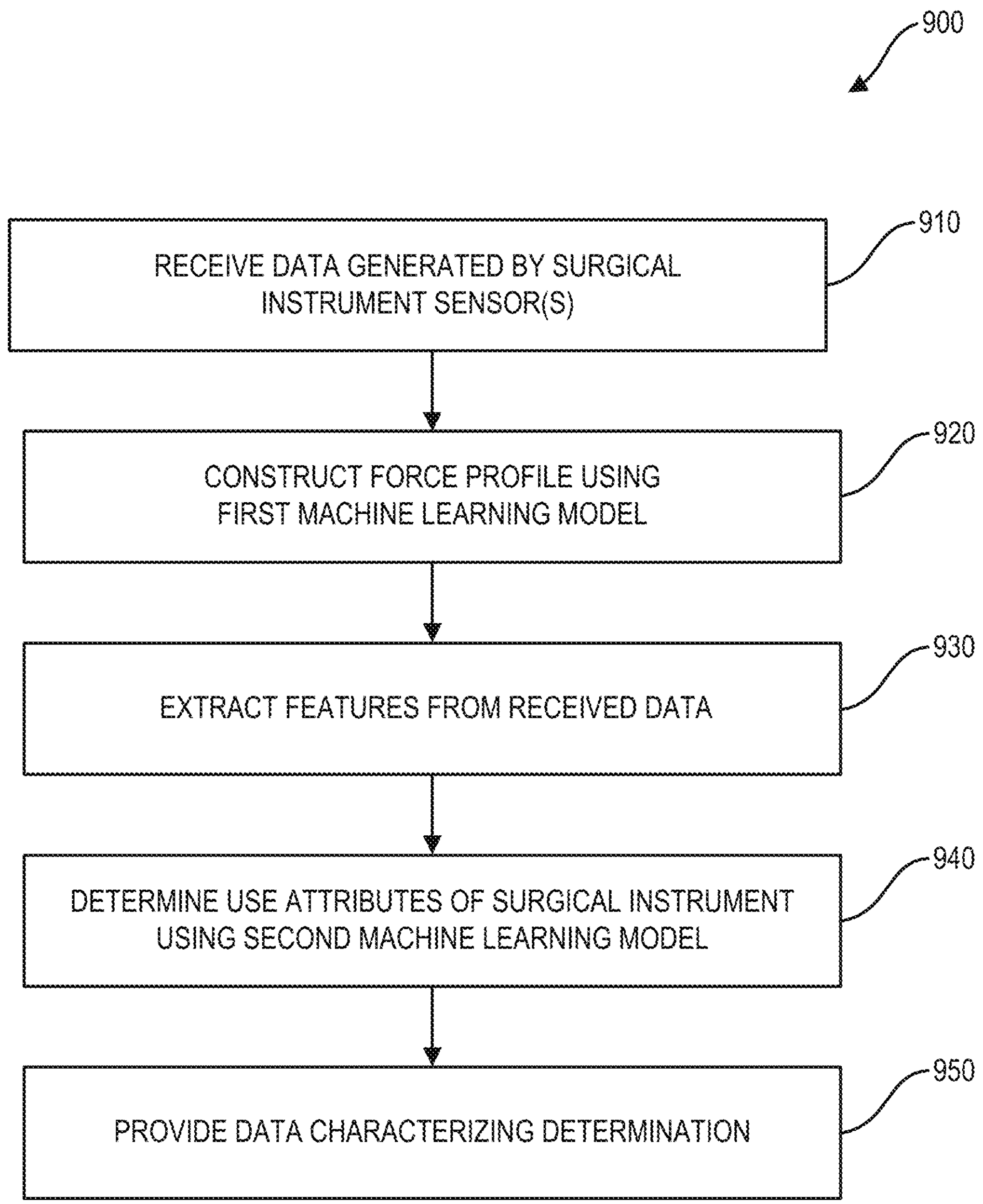
FIG. 9 is a process flow diagram illustrating the characterization of use of a surgical instrument using machine learning.

FIG. 9 is a process flow diagram 900 in which, at 910, data is received that is generated by at least one sensor forming part of a surgical instrument which characterizes use of the surgical instrument in relation to a patient. Subsequently, at 920, a force profile is constructed by a force profile segmentation model using the received data that includes a plurality of force patterns. The force profile segmentation model can include at least one first machine learning trained using historical surgical instrument usage data. In addition, at 930, features are extracted from the received data. These extracted features can be used, at 940, by a force profile pattern recognition model which determines one or more attributes characterizing use of the surgical instrument model using the constructed force profile. The force profile pattern recognition model includes at least one second machine learning model. Data characterizing the determination can, at 950, be provided (e.g., displayed, loaded into memory, stored in physical persistence, transmitted to a remote computing device, etc.), Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, solid state drives, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:

1. A computer-implemented method comprising:

receiving data generated by at least one sensor forming part of a surgical instrument, the at least one sensor characterizing use of the surgical instrument in relation to a patient;

constructing, by a force profile segmentation model using the received data, a force profile comprising a plurality of force patterns, the force profile segmentation model comprising at least one first machine learning trained using historical surgical instrument usage data;

extracting a plurality of features from the received data;

determining, by a force profile pattern recognition model using the constructed force profile and the extracted features, one or more attributes characterizing use of the surgical instrument, the force profile pattern recognition model comprising at least one second machine learning model; and providing data characterizing the determination.

2. The method of claim 1, wherein the surgical instrument is handheld.

3. The method of claim 1, wherein the surgical instrument is at least partially manually operable.

4. The method of claim 1, wherein the surgical instrument is robotic or forms part of a robotic-arm.

5. The method of claim 1, wherein the at least one sensor comprises one or more of: an identification sensor, a force sensor, a motion sensor, a position sensor, an accelerometer, or an optical sensor.

6. The method of claim 1, wherein the surgical instrument comprises forceps with right and/or left prongs having a sensor embedded or affixed thereto.

7. The method of claim 1, wherein the at least sensor generates time-series based data characterizing use of the surgical instrument.

8. The method of claim 1 further comprising:

reducing noise in the received data prior the extraction of the features and/or use by the force profile segmentation model.

9. The method of claim 8, wherein the noise is reduced using a low-pass filter.

10. The method of claim 1 further comprising:

removing outliers in the received data prior to the extraction of the features.

11. The method of claim 1, wherein the force profile segmentation model comprises:

an encoder network followed by a decoder network.

12. The method of claim 1, wherein the received data comprises a waveform and the extracted features characterize one or more of: maximum, range, coefficient of variance, peak counts, peak values, cycle length, signal fluctuations, entropy, and flat spots.

13. The method of claim 1, wherein force profile pattern recognition model comprises at least one neural network.

14. The method of claim 1, wherein the data characterizing the determination identifies a surgical task performed using the surgical instrument.

15. The method of claim 1, wherein the data characterizing the determination identifies a skill level associated with use of the surgical instrument.

16. The method of claim 15, wherein the data characterizing the determination identifies a skill level associated with a particular surgical task using the surgical instrument.

17. The method of claim 1, wherein at least one of the at least one first machine learning model and the at least one second machine learning model is trained using data generated from a single type of surgical instrument.

18. The method of claim 1, wherein at least one of the at least one first machine learning model and the at least one second machine learning model is trained using data generated from a single surgeon.

19. The method of claim 1, wherein at least one of the at least one first machine learning model and the at least one second machine learning model is trained using data generated from a plurality of surgeons.

20. The method of claim 1, wherein the surgical instrument comprises an identification element.

21. The method of claim 20 further comprising:

associating the identification element with one of a plurality of machine learning models; and selecting at least one of the at least one first machine learning model and the at least one second machine learning model from the plurality of available machine learning models based on the associating.

22. The method of claim 21, wherein the identification element comprises a radio frequency identification (RFID).

23. The method of claim 1, wherein providing data characterizing the determination comprises one or more of: causing the data characterizing the determination to be displayed in an electronic visual display, storing the data characterizing the determination in physical persistence, loading the data characterizing the determination in memory, or transmitting the data characterizing the determination to a remote computing system.

24. The method of claim 1, wherein the provided data characterizes one or more of: a completion time for a surgical task, a range of force applications in connection with a surgical task, a force variability index, or a force uncertainty index compared to one or more other surgical instrument users.

25. The method of claim 1, wherein the provided data comprises conveying feedback to a user of the surgical instrument.

26. The method of claim 25, wherein the conveyed feedback comprises one or more of: haptic, visual, or audio feedback.

27. The method of claim 1, wherein the feedback is conveyed on a heads-up display worn or in view of a user of the surgical instrument.

28. The method of claim 1, wherein at least one of the force profile segmentation model or the force profile recognition model is trained on an endpoint computing instrument executing both such models.

29. The method of claim 1, wherein at least one of the force profile segmentation model or the force profile recognition model is trained at least on part by a cloud-based computing service.

30. The method of claim 1 further comprising:
anonymizing features extracted from the data;
encrypting the anonymized features; and
transmitting the encrypted, anonymized features to a remote computing system to train one or more models corresponding to at least one of the force profile segmentation model or the force profile recognition model.

* * * * *